(12) United States Patent
Knodel

(10) Patent No.: US 9,320,519 B1
(45) Date of Patent: Apr. 26, 2016

(54) SINGLE-TRIGGER CLAMPING AND FIRING OF SURGICAL STAPLER

(75) Inventor: Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 998 days.

(21) Appl. No.: 13/094,805

(22) Filed: Apr. 26, 2011

(51) Int. Cl.
*A61B 17/068* (2006.01)
*A61B 17/072* (2006.01)
*A61B 17/28* (2006.01)

(52) U.S. Cl.
CPC .............. *A61B 17/068* (2013.01); *A61B 17/072* (2013.01)

(58) Field of Classification Search
CPC ............ A61B 2017/2946; A61B 2017/00367; A61B 2017/00371; A61B 2017/00424; A61B 2017/00982; A61B 2017/2917; A61B 2017/2923; A61B 2019/4805; A61B 17/2833; A61B 17/07207; A61B 17/12013; A61B 17/2909; A61B 17/068; A61B 17/072
USPC ....................... 227/175.1, 175.2, 177.1, 176.1
See application file for complete search history.

(56) References Cited

U.S. PATENT DOCUMENTS

| | | | |
|---|---|---|---|
| 2,127,665 A | 8/1938 | Leslie | |
| 3,581,551 A | 6/1971 | Wilkinson | |
| 3,650,453 A | 3/1972 | Smith, Jr. | |
| 3,675,688 A | 7/1972 | Bryan et al. | |
| 3,717,294 A | 2/1973 | Green | |
| 3,837,555 A | 9/1974 | Green | |
| 3,899,914 A | 8/1975 | Akiyama | |
| 3,955,581 A | 5/1976 | Spasiano et al. | |
| 4,043,504 A | 8/1977 | Hueil et al. | |
| 4,086,926 A | 5/1978 | Green et al. | |
| 4,127,227 A | 11/1978 | Green | |
| 4,228,895 A | 10/1980 | Larkin | |
| 4,275,813 A | 6/1981 | Noiles et al. | |
| 4,475,679 A | 10/1984 | Fleury, Jr. | |
| 4,523,707 A | 6/1985 | Blake, III et al. | |
| 4,556,058 A | 12/1985 | Green | |
| 4,589,416 A | 5/1986 | Green | |
| 4,633,861 A | 1/1987 | Chow et al. | |
| 4,655,222 A | 4/1987 | Florez et al. | |
| 4,719,917 A | 1/1988 | Barrows et al. | |
| 4,762,260 A | 8/1988 | Richards et al. | |

(Continued)

FOREIGN PATENT DOCUMENTS

| | | |
|---|---|---|
| EP | 1238634 | 9/1994 |
| EP | 1464287 | 10/2004 |

(Continued)

OTHER PUBLICATIONS

Gong, Shao W., "Perfectly flexible mechanism and integrated mechanism system design", *Mechanism and Machine Theory 39* (2004), (Nov. 2004), 1155-1174.

(Continued)

*Primary Examiner* — Andrew M Tecco
*Assistant Examiner* — Praachi M Pathak
(74) *Attorney, Agent, or Firm* — Womble Carlyle Sandridge & Rice LLP

(57) ABSTRACT

An exemplary surgical apparatus may include an end effector including a staple holder, an anvil movable relative to the staple holder, and staples held within the staple holder; a shaft extending from the end effector; a handle attached to the shaft, the handle including a single trigger; wherein actuation of the single trigger in a clamping mode clamps the end effector; and wherein actuation of the single trigger in a stapling mode deploys the staples.

13 Claims, 10 Drawing Sheets

(56) References Cited

U.S. PATENT DOCUMENTS

| | | | |
|---|---|---|---|
| 4,969,591 A | 11/1990 | Richards et al. | |
| 4,978,049 A | 12/1990 | Green | |
| 5,156,315 A | 10/1992 | Green et al. | |
| 5,170,925 A | 12/1992 | Madden et al. | |
| 5,192,288 A | 3/1993 | Thompson et al. | |
| 5,242,457 A | 9/1993 | Akopov et al. | |
| 5,269,792 A | 12/1993 | Kovac et al. | |
| 5,307,976 A | 5/1994 | Olson et al. | |
| 5,413,272 A | 5/1995 | Green et al. | |
| 5,415,334 A | 5/1995 | Williamson, IV et al. | |
| 5,456,400 A | 10/1995 | Shichman et al. | |
| 5,476,206 A | 12/1995 | Green | |
| 5,507,776 A | 4/1996 | Hempel | |
| 5,527,319 A | 6/1996 | Green et al. | |
| 5,547,117 A | 8/1996 | Hamblin et al. | |
| 5,547,474 A | 8/1996 | Kloeckl et al. | |
| 5,553,765 A | 9/1996 | Knodel et al. | |
| 5,620,289 A | 4/1997 | Curry | |
| 5,626,585 A | 5/1997 | Mittelstadt et al. | |
| 5,630,541 A | 5/1997 | Williamson, IV et al. | |
| 5,655,698 A | 8/1997 | Yoon | |
| 5,662,260 A | 9/1997 | Yoon | |
| 5,692,668 A | 12/1997 | Schulze et al. | |
| 5,810,855 A | 9/1998 | Rayburn et al. | |
| 5,816,471 A | 10/1998 | Plyley et al. | |
| 5,855,311 A | 1/1999 | Hamblin et al. | |
| 5,871,135 A | 2/1999 | Williamson, IV et al. | |
| 5,875,538 A | 3/1999 | Kish et al. | |
| 5,894,979 A | 4/1999 | Powell | |
| 5,918,791 A | 7/1999 | Sorrentino et al. | |
| 5,964,774 A | 10/1999 | McKean et al. | |
| 6,264,087 B1 | 7/2001 | Whitman | |
| 6,306,149 B1 | 10/2001 | Meade | |
| 6,391,038 B2 | 5/2002 | Vargas et al. | |
| 6,419,682 B1 | 7/2002 | Appleby et al. | |
| 6,443,973 B1 | 9/2002 | Whitman | |
| 6,478,804 B2 | 11/2002 | Vargas et al. | |
| 6,592,597 B2 | 7/2003 | Grant et al. | |
| 6,602,252 B2 | 8/2003 | Mollenauer | |
| 6,716,232 B1 | 4/2004 | Vidal et al. | |
| 6,817,508 B1 | 11/2004 | Racenet | |
| 6,843,403 B2 | 1/2005 | Whitman | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,111,768 B2 | 9/2006 | Cummins et al. | |
| 7,128,253 B2 | 10/2006 | Mastri et al. | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,258,262 B2 | 8/2007 | Mastri et al. | |
| 7,401,720 B1 | 7/2008 | Durrani | |
| 7,434,715 B2 | 10/2008 | Shelton, IV et al. | |
| 7,467,740 B2 | 12/2008 | Shelton, IV et al. | |
| 7,497,865 B2 | 3/2009 | Willis et al. | |
| 7,506,791 B2 | 3/2009 | Omaits et al. | |
| 7,517,356 B2 | 4/2009 | Heinrich | |
| 7,588,177 B2 | 9/2009 | Racenet | |
| 7,604,151 B2 | 10/2009 | Hess et al. | |
| 7,635,073 B2 | 12/2009 | Heinrich | |
| 7,635,373 B2 | 12/2009 | Ortiz | |
| 7,641,432 B2 | 1/2010 | Lat et al. | |
| 7,644,848 B2 | 1/2010 | Swayze et al. | |
| 2003/0120284 A1 | 6/2003 | Palacios et al. | |
| 2003/0236551 A1 | 12/2003 | Peterson | |
| 2005/0103819 A1* | 5/2005 | Racenet et al. | 227/175.1 |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2006/0241660 A1 | 10/2006 | Bombard et al. | |
| 2006/0253143 A1 | 11/2006 | Edoga | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |
| 2007/0175950 A1 | 8/2007 | Shelton, IV et al. | |
| 2008/0078807 A1 | 4/2008 | Hess et al. | |
| 2008/0272175 A1 | 11/2008 | Holsten et al. | |
| 2008/0296345 A1* | 12/2008 | Shelton et al. | 227/176.1 |
| 2009/0065552 A1* | 3/2009 | Knodel et al. | 227/180.1 |
| 2009/0145947 A1* | 6/2009 | Scirica et al. | 227/175.2 |
| 2010/0179559 A1 | 7/2010 | Walker | |

FOREIGN PATENT DOCUMENTS

| | | |
|---|---|---|
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004), 265-272.

Kolios, Efrossini et al., "Microlaparoscopy", *J. Endourology* 18(9), (Nov. 2004),811-817.

Steichen, Felicien M., et al., "Mechanical Sutures in Surgery", *Brit. J. Surg.* 60(3), (Mar. 1973),191-197.

"Notification of Transmittal of the International Search Report and the Written Opinion of the International Searching Authority", PCT/US2008/075449, (Apr. 29, 2009).

"International Search Report", PCT/US2008/075449, (Apr. 29, 2009).

"Written Opinion of the International Searching Authority", PCT/US2008/075449, (Apr. 29, 2009).

"Cardica Microcutter Implant Delivery Device 510(k), Cover Sheet, Table 10.1, "Substantial Equivalence Comparison," and Section 12, "Substantial Equivalence Discussion"".

* cited by examiner

SINGLE-TRIGGER CLAMPING AND FIRING OF SURGICAL STAPLER

FIELD OF THE INVENTION

The invention generally relates to surgical instruments, and more specifically to the actuation of surgical instruments.

BACKGROUND

Minimally invasive surgery is performed through small incisions in the body, into which trocar ports may or may not be placed. One or more surgical instruments are inserted through each incision in order to perform the surgical procedure. In order to effectuate one of the objectives of minimally invasive surgery, which is the minimization of incisions to the body to reduce healing time and scarring, it is desirable to minimize the number of incisions made in the body. The number of incisions and their placement are determined by the particular surgical procedure to be performed and the configuration of the instruments used to carry out that procedure.

One problem encountered during the performance of surgical stapling in a minimally-invasive procedure, or even an open surgical procedure, is the need for different triggers on a surgical stapler for clamping and for staple deployment. The use of multiple triggers increases the complexity of use of, the part count of, and the size of a surgical stapler.

BRIEF DESCRIPTION OF THE DRAWINGS

The use of the same reference symbols in different figures indicates similar or identical items.

DETAILED DESCRIPTION

U.S. Patent Application Publication No. 2009/0065552, published on Mar. 12, 2009 (the "Endocutter Document"), is hereby incorporated by reference herein in its entirety.

Figure 1:
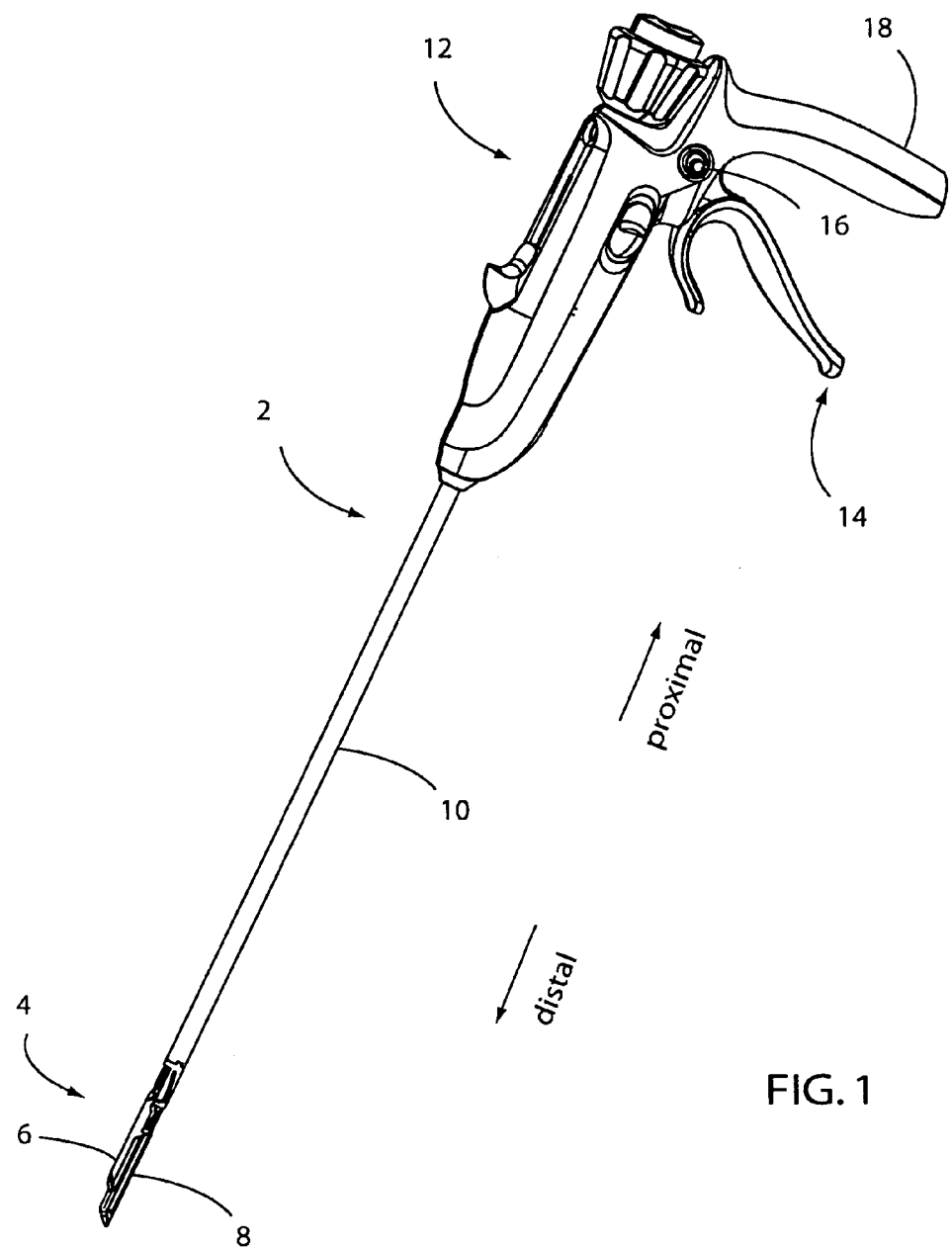
FIG. 1 is a perspective view of a surgical stapler.

Referring to FIG. 1, an exemplary surgical stapler 2 may include an end effector 4, which in turn includes a staple holder 8 and an anvil 6, where at least one of the staple holder 8 and the anvil 6 are rotatable and/or otherwise movable relative to one another. Alternately, the staple holder 8 and the anvil 6 may be directly connected to one another in any other suitable manner, if desired. The staple holder 8 and anvil 6 may be configured substantially as set forth in the Endocutter Document. The staple holder 8 and anvil 6 may be fabricated from any suitable material or materials. As one example, both the staple holder 8 and anvil 6 may be fabricated from stainless steel. As another example, at least one of the staple holder 8 and anvil 6 may be fabricated at least in part from a ceramic material, to provide enhanced stiffness. As another example, the end effector 4 may be any other suitable item for treating or visualizing tissue, such as but not limited to at least one electrode (bipolar or otherwise), adhesive applicator, camera, ultrasound emitter, forceps, or other items. The end effector 4 may be connected to the distal end of a shaft 10. The shaft 10 may be rigid along part or all of its length, and/or may include an articulating region, such as described in U.S. patent application Ser. No. 12/400,760, filed on Mar. 9, 2009 (the "Articulation Document"), which is hereby incorporated by reference in its entirety.

The handle 12 may be attached to the proximal end of the shaft 10, or any other suitable portion of the shaft 10. The shaft 10 may be fabricated integrally with the handle 12. Alternately, the shaft 10 and the handle 12 may be two separate items that are connected together in any suitable manner. The handle 12 may include any mechanism, mechanisms, structure or structures that are suitably configured to actuate the end effector 4. The handle 12 may be actuated purely by hand, meaning that the handle 12 mechanically converts force applied thereto by hand to force utilized to actuate the end effector 4. As another example, the handle 12 may include a source of stored energy for actuating the end effector 4. The source of stored energy may be mechanical (such as a spring), electrical (such as a battery), pneumatic (such as a cylinder of pressurized gas) or any other suitable source of stored energy. The source of stored energy, its regulation, and its use in actuating the end effector 4 may be as described in commonly-assigned U.S. Pat. No. 7,682,368, issued on Mar. 23, 2010, which is herein incorporated by reference in its entirety. The handle 12 may instead, or also, include a connector or connectors suitable for receiving stored energy from an external source, such as a hose connected to a hospital utility source of pressurized gas or of vacuum, or an electrical cord connectable to a power source.

The handle 12 may include a trigger 14 and a mode button 16. Advantageously, the handle 12 includes a single trigger 14. The single trigger 14 both clamps the end effector 4 and deploys staples from the staple holder 8, as described in greater detail below. The handle 12 may include a palm grip 18 located proximal to the trigger 14. The palm grip 18 and trigger 14 may be configured such that a user can hold the palm grip 18 against his or her hand, and grasp a distal surface of the trigger 14 with one or more fingers of that hand. Alternately, the handle 12 and trigger 14 may be arranged in any other suitable manner.

Figure 2:
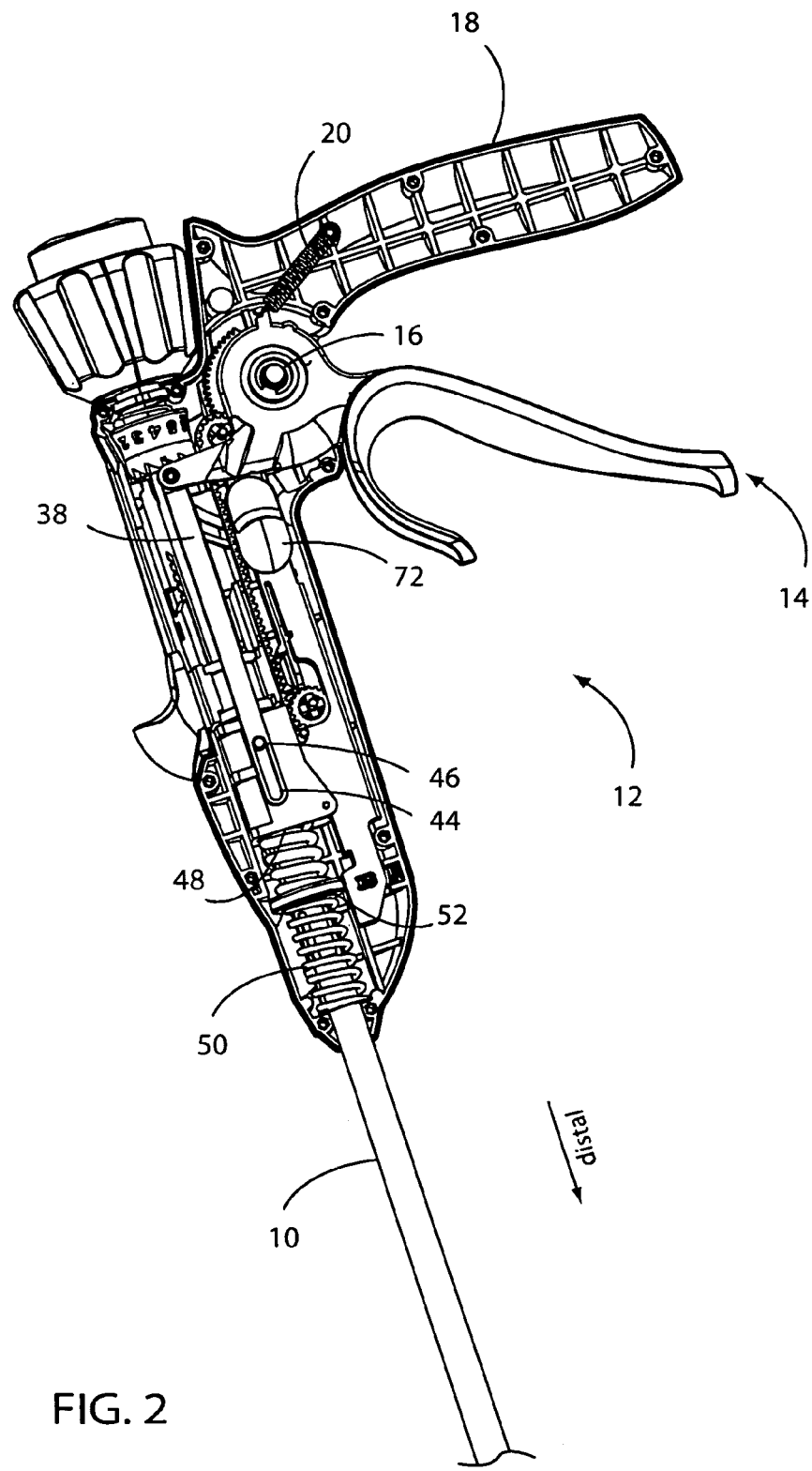
FIG. 2 is a cutaway view of the stapler of FIG. 1.

Referring also to FIG. 2, the trigger 14 may rotate about the mode button 16. As another example, the trigger 14 may rotate about an axis that is substantially collinear with the axis of the mode button 16. The trigger 14 may be connected to the palm grip 18 by a spring 20 that acts to pull the trigger 14 to a neutral position in which the trigger 14 is spaced apart from the palm grip 18. However, the spring 20 may be omitted if desired. As show in FIG. 2, the surgical stapler 2 is in a first configuration, prior to clamping.

Figure 3:
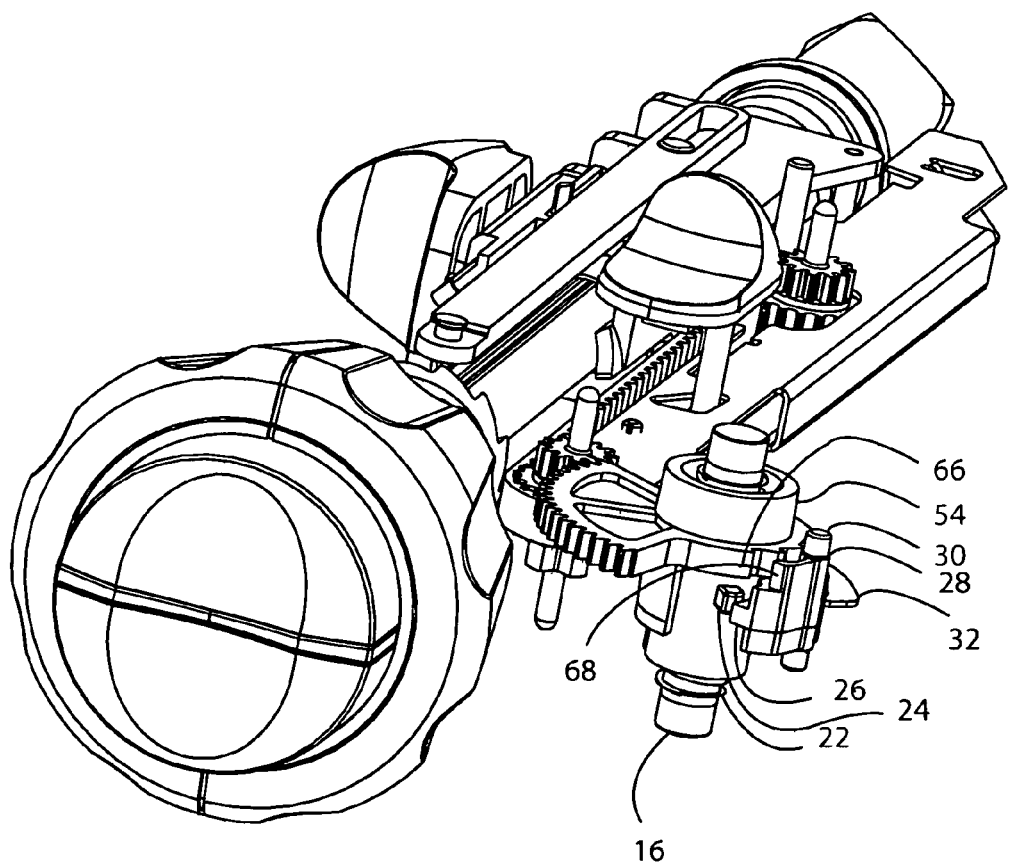
FIG. 3 is a perspective cutaway view of a mode button of the stapler of FIG. 1.
Figure 6:
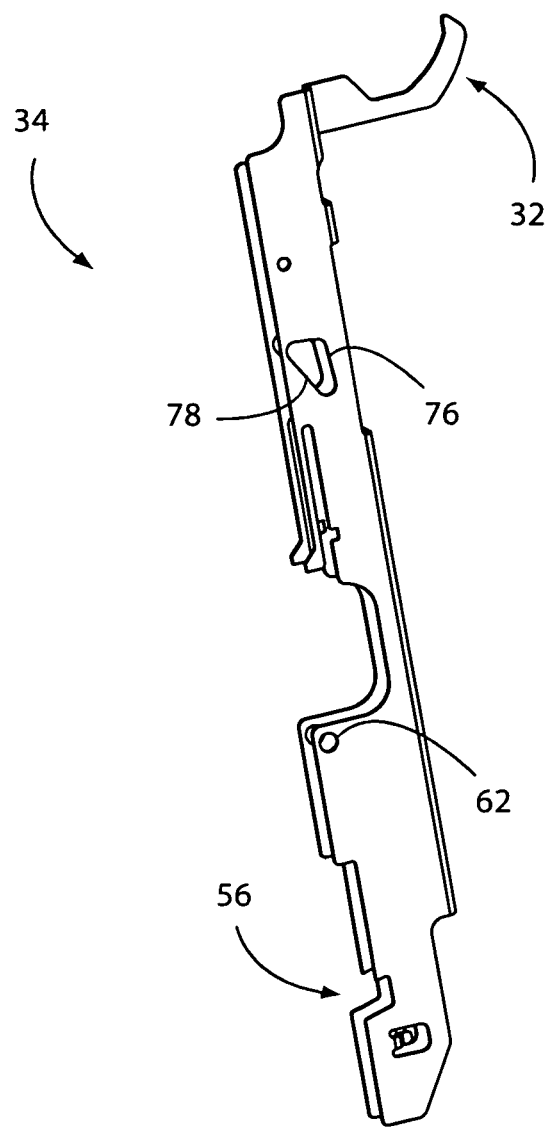
FIG. 6 is a perspective view of a clamp structure.

Referring also to FIG. 3, the mode button 16 may extend substantially laterally relative to the handle 12. A spring 22 may wrap around the mode button 16 to bias the mode button 16 to the neutral position shown in FIG. 3. Both ends of the spring 22 may press against an interior surface of the handle 12 or other structure or mechanism within the handle 12 in order to bias the mode button 16 to the neutral position. A tooth 24 may extend from the mode button 16. The tooth 24 may be substantially cubic in shape. As another example, the tooth 24 may have any other suitable shape. The tooth 24 may extend substantially radially from the mode button 16, which may be generally cylindrical in shape. Alternately, the tooth 24 may extend in any other suitable direction from the mode button 16. The tooth 24 may engage a corresponding rocker tooth 26 fixed to a rocker 28. The rocker 28 may pivot about a rocker axle 30 that is held in place within the handle 12. The portion of the rocker 28 proximal to the rocker axle 30 may be biased upward into engagement with the mode button 16 by a spring 31. Alternately, the spring 31 may be omitted. Referring also to FIG. 6, a hook 32 may be located below the portion of the rocker 28 proximal to the rocker axle 30, and may be spaced apart from the rocker 28 prior to clamping. The hook 32 may extend proximally and downward from a clamp structure 34. The hook 32 acts as a lockout to prevent deployment of staples prior to clamping, as described in greater detail below.

Figure 10:
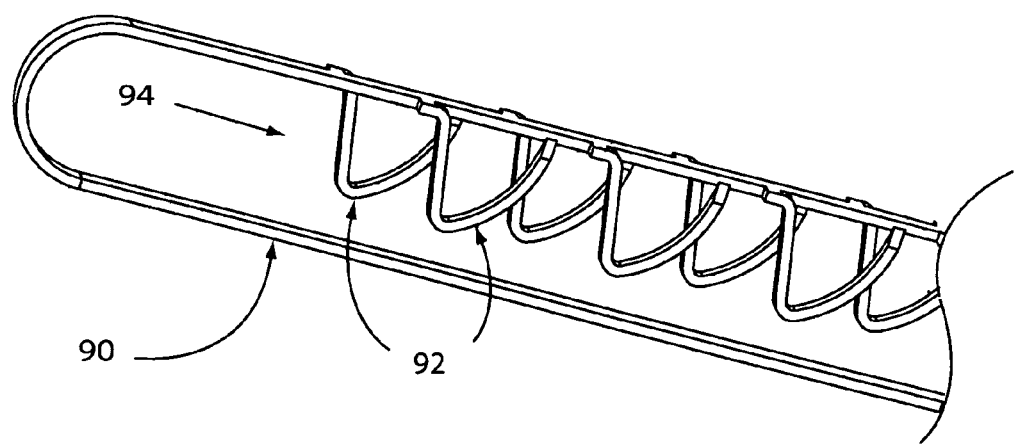
FIG. 10 is a perspective view of staples that are integral with a feeder belt.

Referring also to FIG. 10, a portion of at least one feeder belt 90 may extend from the shaft 10 into, or be positioned within, the end effector 4. The feeder belt 90 and its associated hardware may be as set forth in U.S. patent application Ser. No. 11/851,379, filed Sep. 6, 2007; U.S. patent application Ser. No. 11/956,988, filed Dec. 14, 2007; and U.S. patent application Ser. No. 12/263,171, filed Oct. 31, 2008 (the "Endocutter Documents"), which are herein incorporated by reference in their entirety. In the interest of brevity, the feeder belt 90 will not be described in detail herein. Each feeder belt 90 may be a long, narrow, thin strip of material from which one or more staples 92 extend. At least one staple 90 may be integral with the feeder belt 90, and frangibly connected to the feeder belt 90 at one end, with the other end of the staple being free. One row 94 of staples 92 may be located along each side of the feeder belt 90. Each feeder belt 90 may be movable relative to the end effector 4, as set forth in the Endocutter Applications, such that the end effector 4 can be actuated multiple times without the need to exchange cartridges or remove the end effector 4 from the patient between actuations. The end effector 4 may be configured generally as set forth in the Endocutter Documents, as one example, or may be configured differently.

Figure 5:
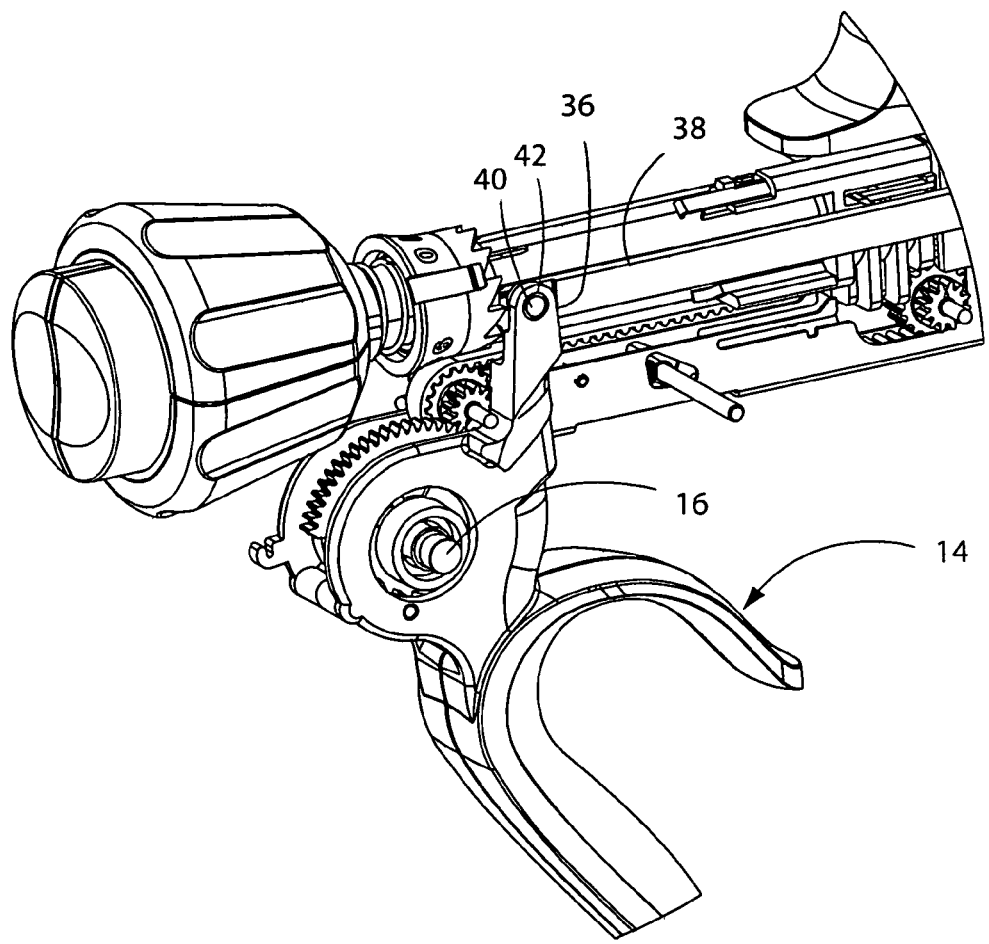
FIG. 5 is a detail cutaway view of a handle of the stapler of FIG. 1.

Referring also to FIGS. 2 and 5, to clamp the end effector 4, the user grasps the trigger 14 and moves the trigger 14 closer to the palm grip 18. The trigger 14 rotates about the axis of the mode button 16. As it does so, at least one arm 36 of the trigger 14 rotates with the trigger 14. Each arm 36 is coupled to a trigger arm 38. Each trigger arm 38 may include a pin 40 at or near its proximal end. Each pin 40 is received in a corresponding aperture 42 in the arm 36 of the trigger 14. In this way, the rotary motion of the trigger 14 during its actuation is converted in part to linear motion of the trigger arm or arms 38 in the distal direction. Referring to FIG. 2, as each trigger arm 38 moves distally, each trigger arm 38 acts to clamp the end effector 4. Such clamping may be performed in any suitable manner, and with any suitable mechanism or mechanisms. As one example, as the trigger 14 is actuated at least one trigger arm 38 moves distally. At least one trigger arm 38 may include a clamp aperture 44 defined longitudinally at or near its distal end. A clamp pin 46 may extend into the clamp aperture 44. The clamp pin 46 may be associated with a clamp assembly 48, where the clamp assembly 48 may include a rod or other mechanism that extends from the handle 12 through the shaft 10 to the end effector 4. Clamping of an end effector 4 is described in, for example, commonly-assigned U.S. patent application Ser. No. 12/263,171, filed on Oct. 31, 2008; Ser. No. 12/612,614, filed on Nov. 4, 2009; and Ser. No. 12/840,156, filed on Jul. 20, 2010 (the "Clamping Documents"), all of which are herein incorporated by reference in their entirety. Optionally, the clamp assembly 48 may be biased proximally by a spring 50 held between an inner surface of the handle 12 and a ring 52 extending outward from the clamp assembly 48. In this way, the end effector 4 optionally may be biased to an unclamped state. As at least one trigger arm 38 moves distally, the clamp pin 46 of the clamp assembly 48 may be located initially at the proximal end of the clamp aperture 44 of that trigger arm 38. As a result, distal motion of at least one trigger arm 38 pushes the clamp pin 46 distally, thereby moving the clamp assembly 48. As a result of the distal motion of the clamp assembly 48, the anvil 6 moves toward the staple holder 8 to clamp the end effector 4, in a manner such as set forth in one or more of the Clamping Documents. As another example, at least one trigger arm 38 may extend through the shaft 10 from the handle 12 to the end effector 4.

As seen most clearly in FIG. 3, the actuation of the trigger 14 initially causes clamping of the end effector 4 because engagement between the tooth 24 and rocker tooth 26 holds off the rocker 28 from a deployment gear 54. Because the rocker 28 and trigger 14 thus do not engage the deployment gear 54, the arm 36 of the trigger 14 acts to clamp the end effector 4 rather than deploy staples 90 from the staple holder 8.

Figure 7:
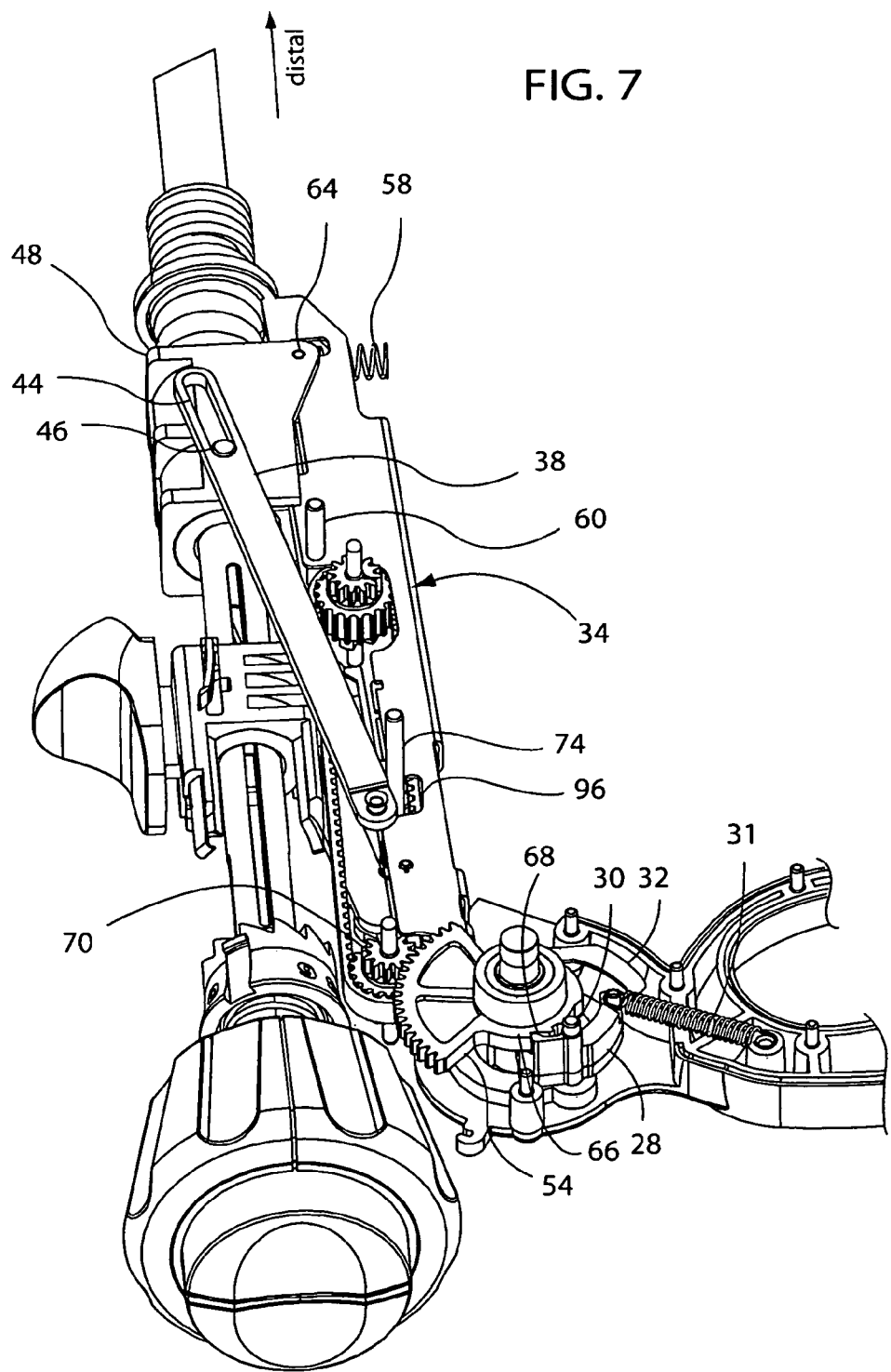
FIG. 7 is a detail cutaway view of a handle of the stapler of FIG. 1, in a clamped configuration.

As the trigger arm or arms 38 continue to advance distally, they may react a distal location at which further distal motion is not possible. However, the trigger 14 may continue to be depressed, and the trigger arm or arms 38 may continue to advance distally. Referring to FIGS. 6-7, the clamp pin 46 of the clamp assembly still may be located at the proximal end of the clamp aperture 44 of at least one trigger arm 38. As that clamp aperture 44 continues to push distally on the clamp pin 46, the force exerted on the clamp pin 46 no longer urges the clamp pin 46 distally. Instead, that force converts to a moment, in part due to the angle from horizontal that the trigger arm 38 has achieved as a result of rotation of the trigger 14 and the associated arms 36 to which the trigger arms 38 are connected. Further, a spring 58 may be positioned between an inner surface of the handle 12 and a distal end of the clamp structure 34. The clamp structure 34 may be pivotable about an axle 60 that may extend generally laterally through one or more apertures 62 defined in the clamp structure 34. As a result, the portion of the clamp structure 34 distal to the axle 60 may be biased upward by the spring 58. As a result, continued actuation of the trigger 14 and continued distal force applied to the clamp pin 46 may cause the clamp structure 34 to rock about the axle 60 such that its distal end rises vertically and the proximal end proximal to the axle 60 moves downward vertically.

Figure 4:
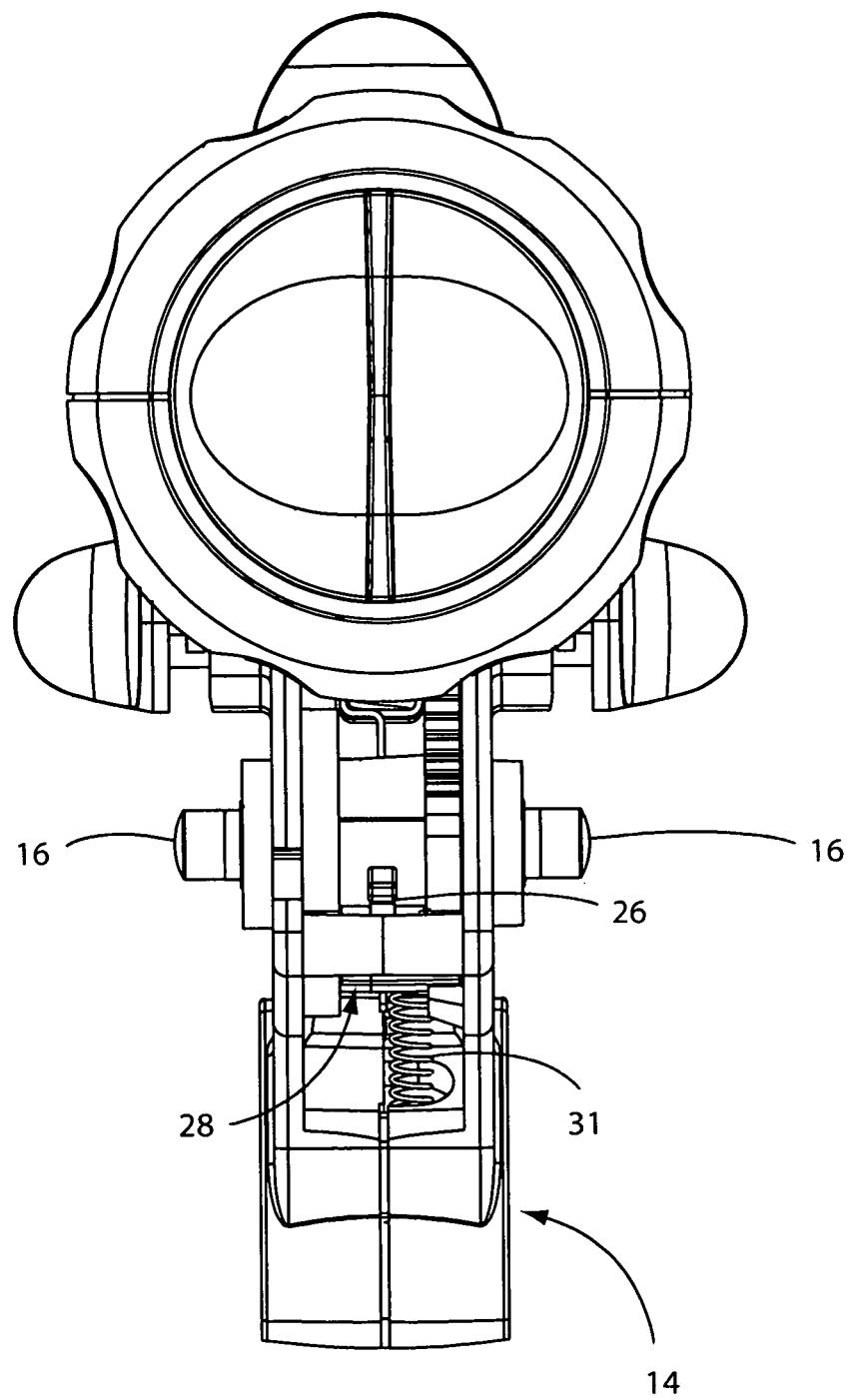
FIG. 4 is a rear view of the mode button of FIG. 3.

After the clamp structure has rocked about the axle 60 such that the proximal end of the clamp structure 34 has moved downward, the hook 32 that extends from the proximal end of the clamp structure 34 has moved downward as well. As a result, referring to FIG. 7, the hook 32 moves downward out of engagement with the rocker 28, such that the hook 32 no longer holds the rocker 28 out of engagement with the deployment gear 54. In this way, the hook 32 may act as a lockout to prevent deployment of staples 90 before clamping of the end effector 4. The hook 32 may engage the rocker 28 on the other side of the rocker axle 30 from the end of the rocker 28 that is configured to engage the deployment gear 54, in order to hold off the rocker 28 from the deployment gear 54. Referring also to FIG. 4, because the rocker 28 is biased about the rocker axle 30 by the spring 31, the rocker 28 is then urged toward engagement with the deployment gear 54. That is, the spring 31 may be fixed at one end to the trigger 14 and at the other end to the rocker 28 on the other side of the rocker axle 30 from the end of the rocker 28 that is configured to engage the deployment gear 54. In this way, the rocker 28 is biased toward engagement with the deployment gear 54. However, the rocker 28 does not move into engagement with the deployment gear 54, due to the engagement between the tooth 24 and rocker tooth 26 holds off the rocker 28 from a deployment gear 54.

Figure 8:
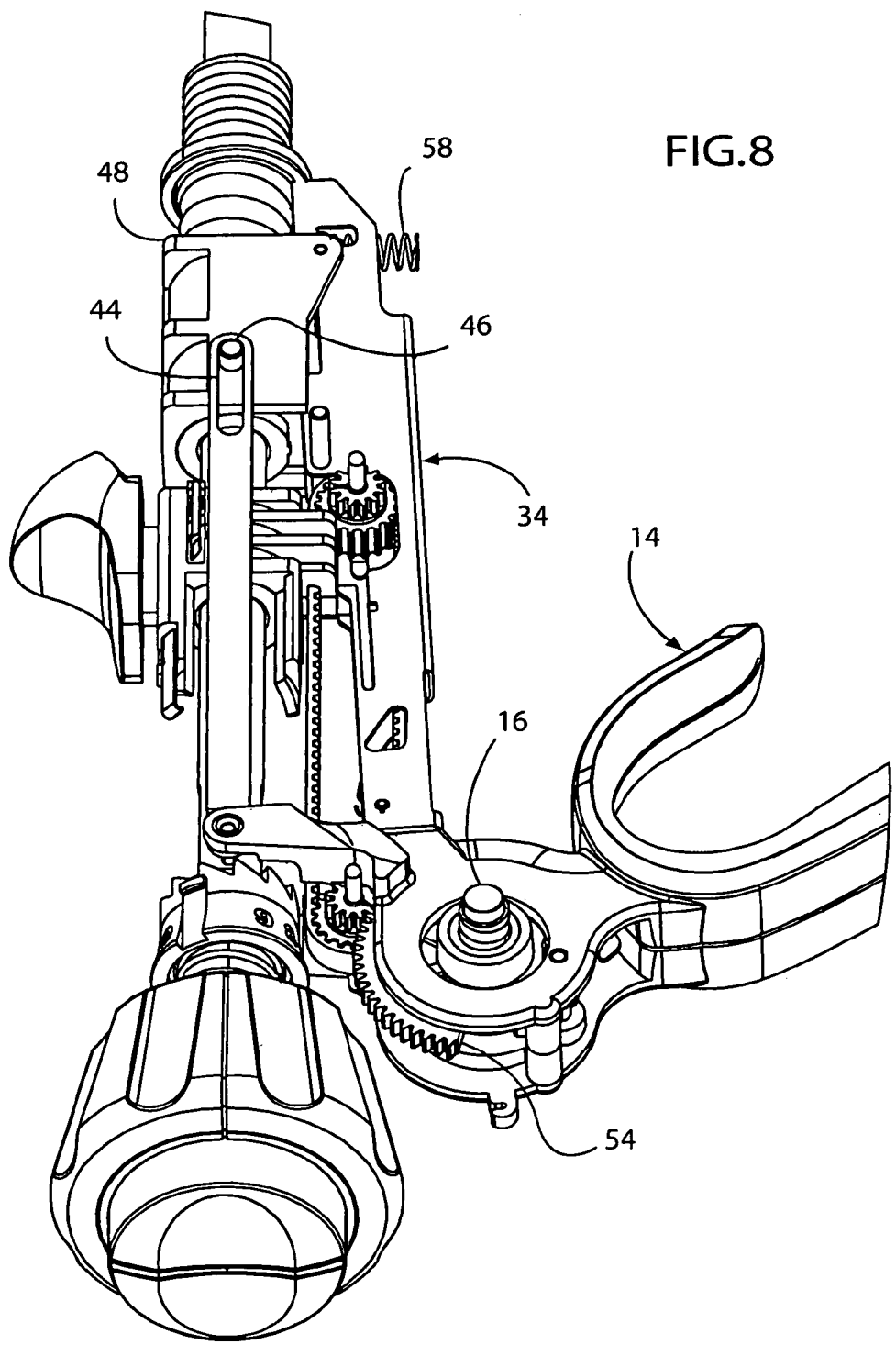
FIG. 8 is a detail cutaway view of a handle of the stapler of FIG. 1, in a position ready for staple deployment.

After clamping, the user may release the trigger 14, which then returns to its original position. However, the end effector 4 remains clamped. Referring also to FIG. 8, as the trigger 14 returns to its original position, the clamp aperture 44 in each trigger arm 38 moves relative to the corresponding clamp pin 46 of the clamp assembly 48. The clamp aperture 44 is long enough to allow motion of the trigger 14 back to its original position such that the clamp pin 46 ends up at, or spaced apart from, the distal end of the clamp aperture 44. As a result, return of the trigger 14 to its original position substantially does not exert force on the clamp pin 46. The clamp assembly 48 may include a crosspin 64 that sits within a trough 56 in the clamp structure 34 distal to the axle 60. Contact between the crosspin 64 and the trough 56 holds the end effector 4 in a clamped position. That is, because the crosspin 64 is held longitudinally in place by the trough 56, due to the upward rock of the clamp structure 34, the crosspin 64 holds the clamp assembly 48 in place and keeps the end effector 4 clamped. Alternately, the crosspin 64 may be omitted, and a different feature of the clamp assembly 48 may reside within the trough 56. Alternately, the trough may be omitted altogether.

Figure 9:
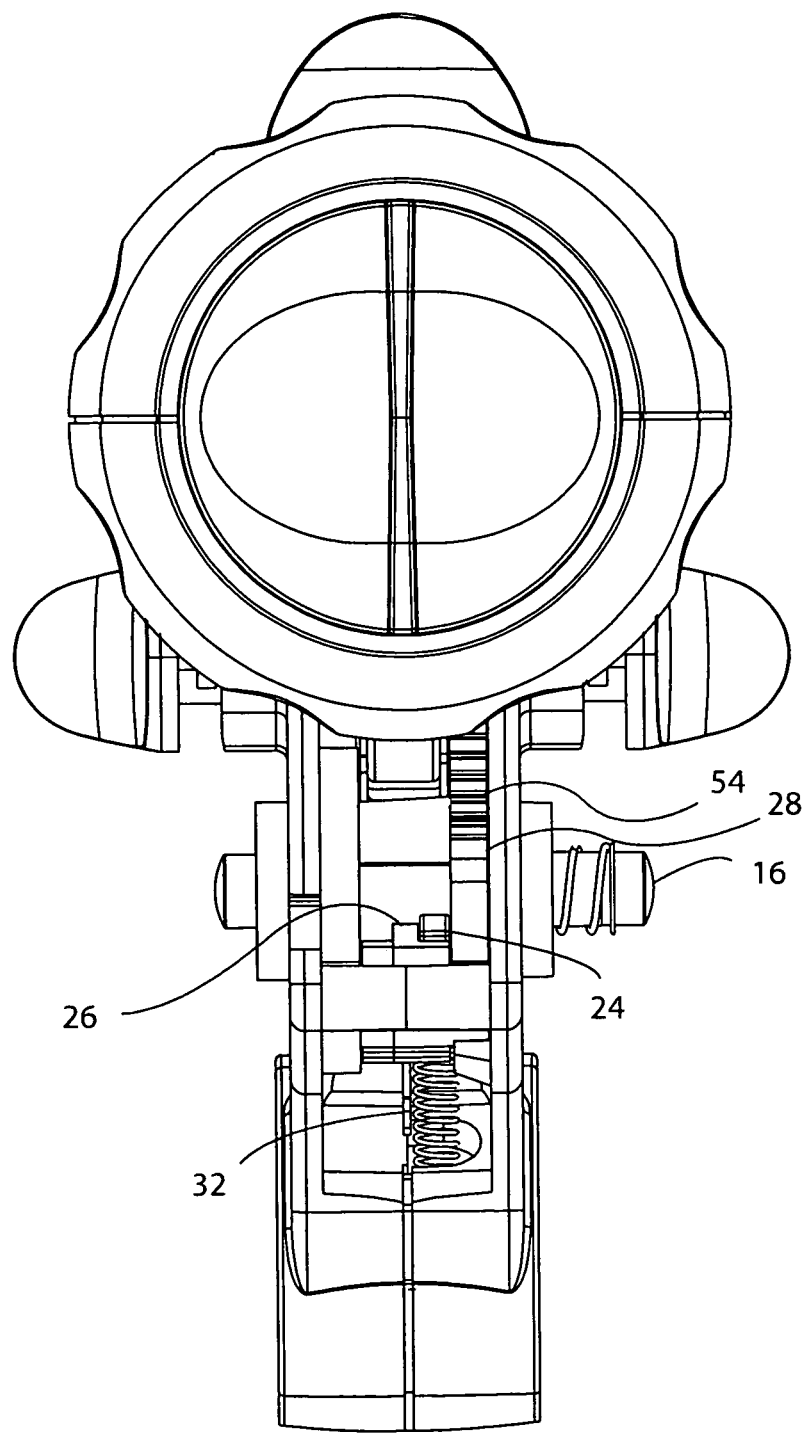
FIG. 9 is a rear view of the mode button of FIG. 3, in a position ready for staple deployment.

When the user is ready to deploy staples 90, the user presses the mode button 16 from either side of the handle 12. The mode button 16 may be depressed from either the left side of the handle 12 in the right direction, or from the right side of the handle 12 in the left direction. As a result of this lateral motion of the mode button, the tooth 24 is moved out of engagement with the rocker tooth 26, referring also to FIG. 9. As a result, the rocker tooth 26 no longer holds off the rocker 28 from the deployment gear 54, and the rocker 28 rotates about the rocker axle 30 into engagement with the deployment gear 54. The deployment gear 54 may include one or more outer teeth 66 defined about its outer perimeter. At least a portion of an edge 68 of the rocker 28 may engage one of the outer teeth 66.

The user may then actuate the trigger 14 again to deploy staples 90. The rocker axle 30 may be fixed to the trigger 14. Thus, as the trigger 14 rotates about the mode button 16, the rocker axle 30 rotates about the mode button 16 as well. Consequently, the rocker axle 30 urges the rocker 28 about the mode button 16, which in turn urges the deployment gear 54 into rotation about the mode button 16. As the deployment gear 54 rotates about the mode button 16, it causes deployment of staples from the staple holder 8 in any suitable manner. As one example, the deployment gear 54 transmits motion to gearing 70 that in turn actuates a rod or other structure that extends along the shaft 10 to the end effector 4 to move distally and deploy staples. That rod or other structure may be connected to a wedge that first deforms, then shears, staples 90 from the feeder belt 92. Such a rod or other structure for transmitting force from the handle 12 to the end effector 4 for staple deployment may be as set forth in the Endocutter Document, or in U.S. patent application Ser. No. 13/090,214, filed on Apr. 16, 2011, which is herein incorporated by reference in its entirety.

The end effector 4 is then unclamped. Unclamping may occur automatically at the end of staple deployment, or may occur upon manual input from the user. As one example, referring to FIGS. 2 and 6-7, an unclamp switch 72 may be fixed to an unclamp rod 74, such that proximal motion of the unclamp switch 72 causes the unclamp rod 74 to move proximally. The unclamp rod 74 may extend laterally through an unclamp aperture 76 defined in the clamp structure 34. The unclamp aperture 76 may include an upper surface 78 that slopes downward in the distal direction. Proximal motion of the unclamp rod 74 against that upper surface 78 thus causes the portion of the clamp structure 34 proximal to the axle 60 to lift upward, thereby rocking the portion of the clamp structure 34 proximal to the axle 60 upward. The portion of the clamp structure 34 distal to the axle 60 correspondingly rocks downward, causing the trough 56 to disengage from the crosspin 64. As a result, the clamp assembly 48 is no longer held in place longitudinally, such that the spring 50 urges the clamp assembly 48 back to its initial position, and consequently the end effector 4 returns to its unclamped state.

After the portion of the clamp structure 34 proximal to the axle 60 rocks upward, the hook 32 moves back into engagement with the rocker 28, pushing the rocker 28 out of engagement with the deployment gear 54. The spring 22 wrapped around the mode button 16 can then urge the mode button 16 back to its initial position, in which the tooth 24 and rocker tooth 26 once again hold off the rocker 28 from the deployment gear 54. The feeder belt 90 may be advanced to move fresh staples 92 in place for another deployment. The handle 12 is then ready for another clamping and staple deployment. The switch between clamping mode to stapling mode, and back to clamping mode, has been performed completely mechanically, as described above. However, the switch between clamping mode to stapling mode, and/or from stapling mode to clamping mode, may be made electromechanically or in any other suitable manner.

The operation of the surgical stapler 2 may be carried out in the course of testing at a factory or other location. If so, the user that possesses the surgical stapler 2 may be a technician, machine or text fixture that exercises the surgical stapler 2 in the course of testing. The term "tissue," in the context of testing the surgical stapler 2 only, includes any substance or material used as a substitute for tissue in the course of testing.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. The use of terms such as "upward" and "downward" in this document refers to the orientation of parts on the page for descriptive clarity, and in no way limits the orientation of the device in use. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:
1. A surgical apparatus, comprising:
   an end effector including a staple holder, an anvil movable relative to said staple holder, and a plurality of staples held within said staple holder;
   a shaft extending from said end effector;

a handle attached to said shaft, said handle including a single trigger; and a clamp structure coupled to said handle, said clamp structure having a hook that acts to prevent deployment of said staples before a clamping of said end effector by preventing an engagement of a rocker with a deployment gear;

wherein actuation of said single trigger in a clamping mode clamps said end effector;

and wherein actuation of said single trigger in a stapling mode deploys said staples.

2. The surgical apparatus of claim 1, wherein the plurality of staples are frangibly connected to a feeder belt.

3. The surgical apparatus of claim 2, wherein said feeder belt is advanceable within said staple holder after deployment of said staples.

4. The surgical apparatus of claim 1, further comprising a mode button movable relative to said handle, wherein the position of said mode button switches said trigger between said clamping mode and said stapling mode.

5. The surgical apparatus of claim 4, further comprising
said rocker pivotable about an axle attached to said trigger, a rocker tooth extending from said rocker, and
a tooth extending from said mode switch;
wherein said tooth engages said rocker tooth in clamping mode.

6. The surgical apparatus of claim 5, further comprising said deployment gear rotatable about said mode button, wherein engagement between said tooth and said rocker tooth holds off said rocker from said deployment gear.

7. The surgical apparatus of claim 6, wherein said tooth is movable out of engagement with said rocker tooth to switch said trigger to stapling mode.

8. The surgical apparatus of claim 6, further comprising said clamp structure located in said handle, said clamp structure pivotable about an axle fixed to said handle, wherein said clamp structure includes said hook extending proximally therefrom, such that engagement between said hook and said rocker holds off said rocker from said deployment gear.

9. The surgical apparatus of claim 6, further comprising said clamp structure arranged in said handle, said clamp structure pivotable about an axle fixed to said handle, wherein said clamp structure includes said hook extending proximally therefrom, wherein said hook engages said rocker to lock out said stapling mode until said end effector is clamped.

10. The surgical apparatus of claim 1, wherein switching between clamping mode and stapling mode is performed completely mechanically.

11. A surgical method, comprising:

possessing a surgical tool including an end effector including a staple holder, an anvil movable relative to said staple holder, and a plurality of staples held within said staple holder; a shaft extending from said end effector; and a handle attached to said shaft, said handle including a single trigger;

actuating for a first time said trigger to clamp said end effector, wherein said surgical tool employs a hook to prevent deployment of said staples prior to clamping of said end effector by preventing an engagement of a rocker with a deployment gear; and actuating for a second time said trigger to deploy staples from said staple holder.

12. The surgical method of claim 11, wherein said surgical tool further comprises a feeder belt to which said staples are frangibly connected; further comprising advancing said feeder belt after both said actuating said trigger for a first time and said actuating said trigger for a second time, actuating said trigger a third time to clamp said end effector again, then actuating said trigger a fourth time to deploy staples again from said staple holder.

13. The surgical method of claim 11, further comprising locking out said actuating said trigger to deploy staples from said staple holder until said actuating for a first time has been performed.

\* \* \* \* \*